(12) United States Patent
Higashiisogawa et al.

(10) Patent No.: US 7,382,460 B2
(45) Date of Patent: Jun. 3, 2008

(54) LIGHT SENSOR, AND DETECTING MECHANISM AND LIGHT-MEASURING MECHANISM IN ANALYZING DEVICE

(75) Inventors: Yukio Higashiisogawa, Kyoto (JP); Junichi Oka, Kyoto (JP); Tetsuaki Saiji, Kyoto (JP)

(73) Assignee: Arkray, Inc., Kyoto (JP)

( * ) Notice: Subject to any disclaimer, the term of this patent is extended or adjusted under 35 U.S.C. 154(b) by 317 days.

(21) Appl. No.: 10/537,003

(22) PCT Filed: Nov. 20, 2003

(86) PCT No.: PCT/JP03/14863

§ 371 (c)(1),
(2), (4) Date: May 26, 2005

(87) PCT Pub. No.: WO2004/051317

PCT Pub. Date: Jun. 17, 2004

(65) Prior Publication Data

US 2006/0076523 A1      Apr. 13, 2006

(30) Foreign Application Priority Data

Nov. 26, 2002   (JP)   ............................. 2002-342103
Nov. 26, 2002   (JP)   ............................. 2002-342104

(51) Int. Cl.
*G01N 21/55*        (2006.01)
(52) U.S. Cl. .................................................. 356/445
(58) Field of Classification Search ................ 356/445, 356/446, 402
See application file for complete search history.

(56) References Cited

U.S. PATENT DOCUMENTS 3,016,464 A  *  1/1962  Bailey ........................ 356/3.02

(Continued)

FOREIGN PATENT DOCUMENTS

EP            0 762 110           3/1997

(Continued)

OTHER PUBLICATIONS

Japanese Office Action from the corresponding JP 2002-342104, mailed May 22, 2007.

(Continued)

*Primary Examiner*—Roy M Punnoose
(74) *Attorney, Agent, or Firm*—Hamre, Schumann, Mueller & Larson, P.C.

(57) ABSTRACT

The present invention relates to an analyzing device provided with: a light-measuring mechanism (6) that includes a light-emitting unit for emitting light onto a test tool (7) to analyze a sample and a light-receiving unit for receiving reflection light from the test tool (7); and a detecting mechanism (4) for detecting whether or not the test tool exists in a target area, the mechanism including a light-emitting unit for emitting light onto the test tool (7) and a light-receiving unit for receiving reflection light from the test tool (7). In the light-measuring mechanism (6), the light-emitting unit and light-receiving unit are disposed such that the light emission axis of the light-emitting unit and the light reception axis of the light-receiving unit are parallel or substantially parallel to each other. The detecting mechanism (4) is arranged such that the one or more light-receiving units selectively receive regularly-reflected light from the test tool (7) among the light emitted from the light-emitting unit.

29 Claims, 14 Drawing Sheets

U.S. PATENT DOCUMENTS

| | | | |
|---|---|---|---|
| 4,283,146 A * | 8/1981 | Roussel | 356/445 |
| 4,728,196 A * | 3/1988 | Gerstorfer | 356/446 |
| 4,763,006 A * | 8/1988 | Rau et al. | 250/559.46 |
| 5,160,981 A * | 11/1992 | Hirashima | 356/446 |
| 6,184,991 B1 * | 2/2001 | Soto et al. | 356/446 |
| 6,246,859 B1 * | 6/2001 | Takemura et al. | 399/371 |
| 6,509,919 B1 | 1/2003 | Tehranchi et al. | |

FOREIGN PATENT DOCUMENTS

| | | |
|---|---|---|
| JP | 57-151837 | 9/1982 |
| JP | 60-35244 | 2/1985 |
| JP | 3-81582 | 8/1991 |
| JP | 5-43091 | 6/1993 |
| JP | 6-87522 | 3/1994 |
| JP | 6-201844 | 7/1994 |
| JP | 9-145613 | 6/1997 |
| JP | 2000-89394 | 3/2000 |
| JP | 2000-131405 | 5/2000 |
| JP | 2001-133395 | 5/2001 |
| JP | 2001-141644 | 5/2001 |
| JP | 2001-337005 | 12/2001 |
| JP | 2002-55174 | 2/2002 |
| JP | 2002-154228 | 5/2002 |
| JP | 2002-257837 | 9/2002 |
| JP | 2002-303679 | 10/2002 |

OTHER PUBLICATIONS

Japanese Office Action from the corresponding JP 2002-342104, mailed Sep. 25, 2007.

* cited by examiner

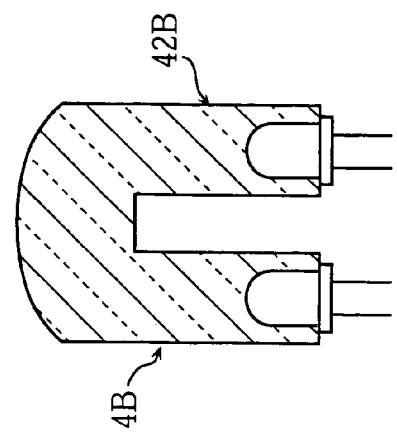
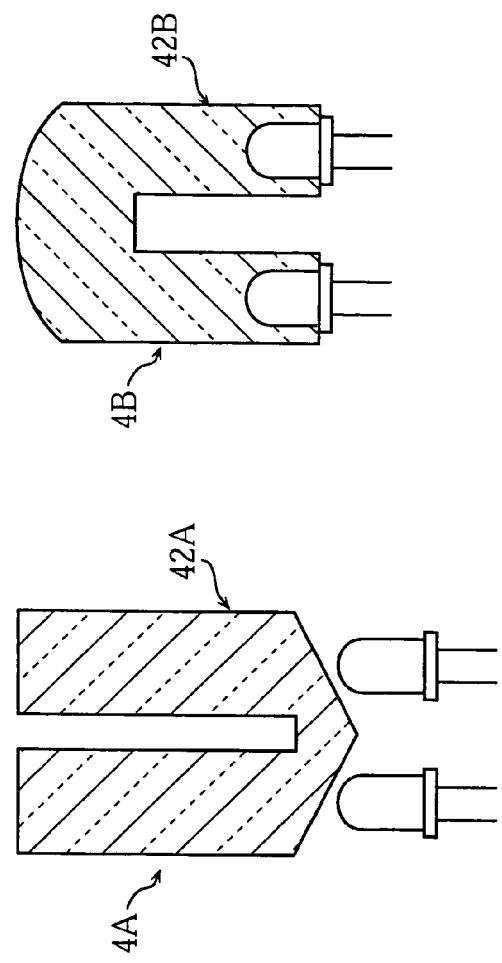
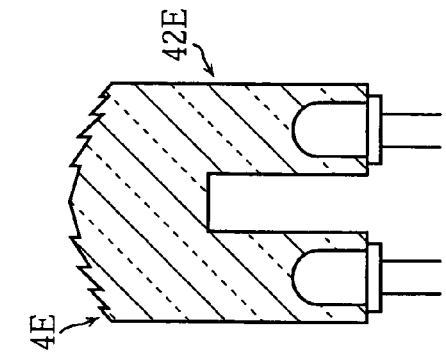
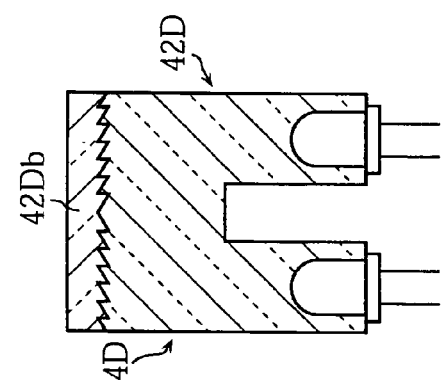
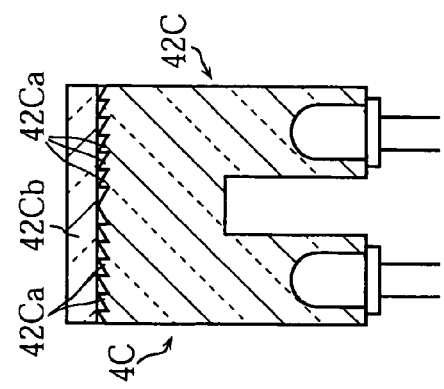

LIGHT SENSOR, AND DETECTING MECHANISM AND LIGHT-MEASURING MECHANISM IN ANALYZING DEVICE

TECHNICAL FIELD

The present invention relates to a technique for analyzing a specific component of a sample with use of a test tool.

BACKGROUND ART

For analyzing a specific component contained in a sample, use may be made of an optical method. An example of such is one that utilizes a color reaction occurring in a test tool. In this kind of analysis, the degree of coloration occurring on the test tool may be checked with eyes. However, when the concentration of a specific component is analyzed quantitatively, an appropriate analyzing device is used.

Some analyzing devices are designed to begin automatic measurement for the amount of specific component after a test tool has been set in the device. Such an analyzing device, as shown in FIG. 17, includes a light source 992 for irradiating a reagent pad 991 of the test tool 990, and a light-receiving unit 993 for receiving the scattered light from the reagent pad 991, whereby analysis of the sample is performed on the basis of the quantity of light received by the light-receiving unit 993 (see JP-A-H09-145613, for example).

In the illustrated example, the test tool 990 is irradiated directly with the light from the light source 992, and the scattered light from the test tool 990 is received directly in the light-receiving unit 993. Hence, for the scattered light from the test tool 990 to be received, the light source 992 and the light-receiving unit 993 need be disposed such that the light reception axis S2 of the light-receiving unit 993 is inclined relative to the light emission axis S1 of the light source 992. Accordingly, the distance between the light source 992 and the light-receiving unit 993 tends to be large, thereby making it difficult to reduce the size of a light-measuring mechanism employing the above method, and hence the size of the analyzing device incorporating the light-measuring mechanism. Moreover, since scattered light is received, the quantity of light received in the light-receiving unit 993 is small. Unfavorably, this increases the likelihood of measurement errors.

Meanwhile, for an analyzing device to perform automatic quantity measurement, the analyzing device needs to recognize that a test tool has been supplied. Typically, such recognition of a test tool is automatically performed in the analyzing device, though it is also possible to arrange that the recognition is initiated by the user operating an operation switch on the device.

Typically, the automatic recognition (detection) of the test tool in the analyzing device is attained through a light sensor. An example of such a light sensor, shown in FIG. 18, uses scattered light from a test tool 994. In the illustrated example, the light source 995 emits light toward a target site in which the test tool 994 is to be placed. When scattered light from the target site is received by the light-receiving unit 996, it is determined that the test tool 994 is placed in the target site.

However, with the above detection method, reflection light is received in the light-receiving unit 996 not only when the test tool 994 is placed in the target site, but also when the user's hand passes over the target site or the test tool 994 is brought above the target site. In such cases, the analyzing device may erroneously recognize that the test tool 994 has been properly set in the target site, and begin an analysis operation.

DISCLOSURE OF THE INVENTION

An object of the present invention is to reduce the size of a light sensor that may be used as a light-measuring mechanism of an analyzing device, and thereby reducing the overall size of the analyzing device incorporating such a light-measuring mechanism.

Another object of the present invention is to prevent erroneous detection in detecting a test tool in an analyzing device employing an optical method.

A first aspect of the present invention provides a light sensor comprising: one or more light-emitting units for emitting light onto a target object; and one or more light-receiving units for receiving reflection light from the target object. The one or more light-emitting units and the one or more light-receiving units are disposed such that a light emission axis of the one or more light-emitting units and a light reception axis of the one or more light-receiving units are parallel or substantially parallel to each other.

A second aspect of the present invention provides a light-measuring mechanism for a test tool, comprising: one or more light-emitting units for emitting light onto a test tool used for analyzing a sample; and one or more light-receiving units for receiving reflection light from the test tool. The one or more light-emitting units and the one or more light-receiving units are disposed such that a light emission axis of the one or more light-emitting units and a light reception axis of the one or more light-receiving units are parallel or substantially parallel to each other.

Preferably, the light sensor or light-measuring mechanism of the present invention may further comprise a light guide for regulating a path of at least one of light traveling toward the target object (test tool) from the one or more light-emitting units and light traveling toward the one or more light-receiving units from the target object (test tool).

Preferably, the light guide may comprise: one or more first entrance areas for introducing light emitted from the one or more light-emitting units into the light guide; one or more first output areas for outputting the light introduced into the light guide toward the target object (test tool); one or more second entrance areas for introducing reflection light from the target object (test tool) into the light guide; and one or more second output areas for outputting the light reflected by the target object (test tool) and then introduced into the light guide toward the one or more light-receiving units. In this instance, at least one area of the one or more first entrance areas, the one or more first output areas, the one or more second entrance areas, and the one or more second output areas may be arranged to refract light passing through the above-mentioned at least one area.

The light guide may comprise a lens or a prism, for example.

The one or more first output areas and the one or more second entrance areas may be formed as planar surfaces that are orthogonal or substantially orthogonal to the light emission axis of the one or more light-emitting units.

The light guide may comprise a core portion extending along the light emission axis, and an outer shell portion having a lower refractive index than the core portion and surrounding the core portion. In this case, the outer shell portion may function as a cladding layer, and thus the entire light guide may be constituted as an optical fiber.

The light guide may also be arranged such that it comprises an optical fiber portion extending along the light emission axis, and an outer shell portion surrounding the optical fiber portion.

The light sensor and the light-measuring mechanism of the present invention may further comprise a light shield for causing light that is reflected by the target object (test tool) at a target angle, among the light reflected by the target object (test tool), to enter the one or more light-receiving units selectively. In this case, the target angle may be set to 45 degrees or substantially 45 degrees, for example.

The light shield may be formed with an opening for selectively exposing the one or more first output areas and the one or more second entrance areas.

The light shield may comprise an annular part surrounding the periphery of at least one of the one or more first output areas and the one or more second entrance areas, for example.

When the one or more first output areas or the one or more second entrance areas of the light guide comprise a plurality of first output areas or a plurality of second entrance areas, the light shield may be formed with an opening for exposing the plurality of first output areas or the plurality of second entrance areas successively.

When the one or more light-emitting units are constituted by a single light-emitting unit, and the one or more light-receiving units are constituted by a plurality of light-receiving units, the plurality of light-receiving units may be disposed so as to surround the single light-emitting unit. When the one or more light-emitting units are constituted by a plurality of light-emitting units, and the one or more light-receiving units are constituted by a single light-receiving unit, the plurality of light-emitting units may be disposed so as to surround the single light-receiving unit. In this case, the plurality of light-emitting units may preferably comprise two or more light-emitting units which emit light having different peak wavelengths.

Preferably, the one or more light-receiving units may be arranged to receive scattered light reflected by the object (test tool) among the light emitted from the one or more light-emitting units.

The light sensor and the light-measuring mechanism of the present invention may comprise a wavelength selection portion for selecting the wavelength of the light to be introduced into the one or more light-receiving units, or may comprise a wavelength selection portion for selecting the wavelength of light emitted from the one or more light-emitting units. The wavelength selection portion may comprise an interference filter or a color filter, for example.

A third aspect of the present invention provides a detecting mechanism of a test tool for detecting whether or not a test tool exists in a target area. The mechanism comprises a light-emitting unit for emitting light toward the target area, and a light-receiving unit for receiving reflection light from the test tool. The light-receiving unit is constituted to receive light that is reflected regularly by the test tool selectively, among the light emitted by the light-emitting unit.

A fourth aspect of the present invention provides a detecting mechanism of a test tool for detecting whether or not a test tool exists in a target area, the mechanism comprising a light-emitting unit for emitting light toward the target area, and a light-receiving unit for receiving reflection light from the test tool. The detecting mechanism is constituted such that at least one of the light traveling toward the target area from the light-emitting unit and the light traveling toward the light-receiving unit from the target area is refracted.

The detecting mechanism of the present invention may further comprise a light guide for regulating the path of at least one of the light traveling toward the target area from the light-emitting unit and the light traveling toward the light-receiving unit from the target area.

The light guide may comprise: a first entrance area for introducing light emitted from the light-emitting unit into the light guide; a first output area for outputting the light introduced into the light guide from the light-emitting unit toward the target area; a second entrance area for introducing reflection light from the test tool into the light guide; and a second output area for outputting the light reflected on the test tool and then introduced into the light guide toward the light-receiving unit. In this case, at least one area of the first entrance area, first output area, second entrance area, and second output area may preferably be constituted to refract light passing through the above-mentioned one area.

The light guide may comprise a prism or a lens, for example. Typically, the light guide comprises a cylindrical lens or a Fresnel lens.

The light guide may comprise a lens having an irregular surface, and a cover used for covering the irregular surface to make flat the upper surface of the light guide. An example of a lens having an irregular surface is a Fresnel lens.

Preferably, the light-emitting unit may comprise a light-emitting diode.

A fifth aspect of the present invention provides an analyzing device comprising: a light-measuring mechanism that includes one or more light-emitting units for emitting light onto a test tool used for analyzing a sample, and one or more light-receiving units for receiving reflection light from the test tool; and a detecting mechanism for detecting whether or not a test tool exists in a target area, including a light-emitting unit for emitting light onto the test tool, and a light-receiving unit for receiving reflection light from the test tool. The one or more light-emitting units and one or more light-receiving units of the light-measuring mechanism are disposed such that a light emission axis of the light-emitting units and a light reception axis of the light-receiving units are parallel or substantially parallel to each other. The light-receiving unit of the detecting mechanism is constituted to receive light that is reflected regularly by the test tool selectively, among the light emitted by the light-emitting unit of the detecting mechanism.

In the present invention, the term "light emission axis" denotes an axis extending in the direction of the largest quantity of emitted light over the distribution of the light quantity emitted from the light-emitting unit. The term "light reception axis" denotes an axis extending along the normal at a point where the quantity of received light is the largest over the the distribution of the light quantity received in the light-receiving unit.

BRIEF DESCRIPTION OF THE DRAWINGS

FIGS. 10A to 10E are sectional views showing other examples of a detecting mechanism;

BEST MODE FOR CARRYING OUT THE INVENTION

Figure 1:
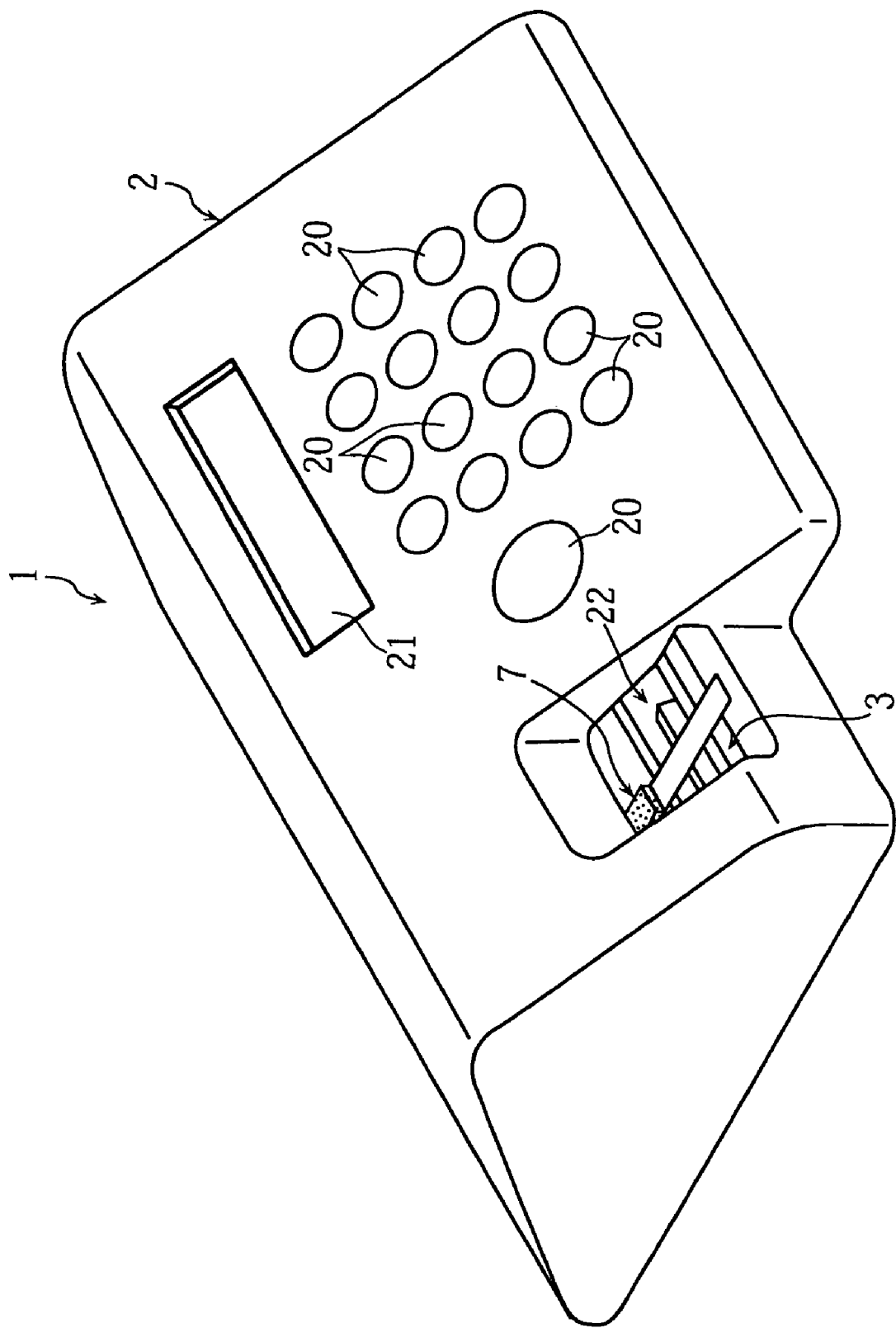
FIG. 1 is an overall perspective view showing an example of an analyzing device according to the present invention.
Figure 2:
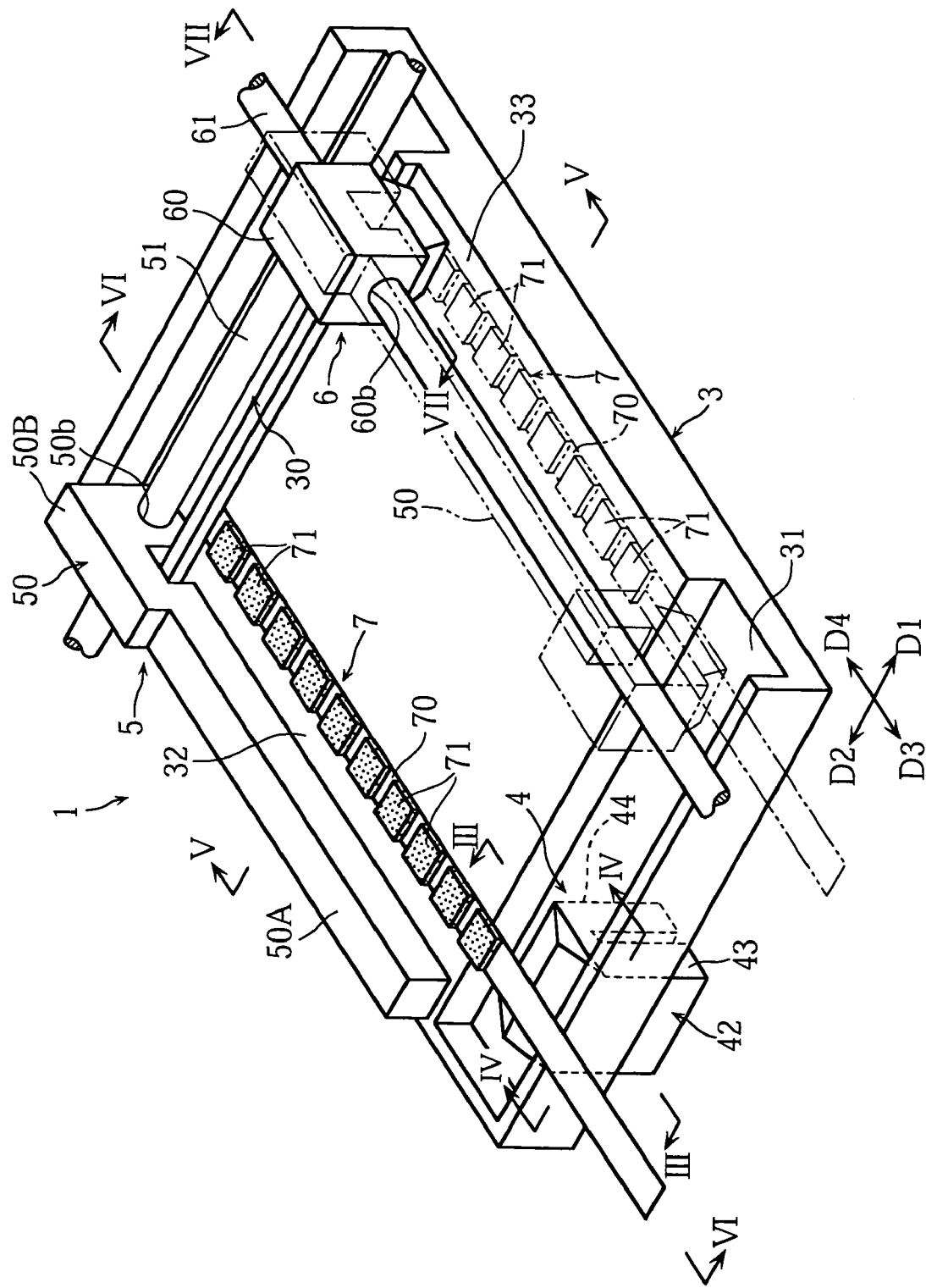
FIG. 2 is a perspective view showing the interior constitution of the analyzing device shown in FIG. 1.

Referring to FIGS. 1 and 2, an analyzing device 1 includes a housing 2, in which a stage 3, a detecting mechanism 4, a conveying mechanism 5, and a light-measuring mechanism 6 are provided. As clearly shown in FIG. 1, a plurality of operating buttons 20 and a display 21 are provided on the housing 2 together with an introduction portion 22 for placing a test tool 7 on the stage 3. The introduction portion 22 is formed as a cutout that communicates with the interior of the housing 2 and exposes a part of the stage 3. As shown in FIG. 2, for the test tool 7, use is made of a strip-like base 70 upon which a plurality of reagent pads 71 are arranged at intervals in the longitudinal direction of the base 70. Each reagent pad 71 contains a reagent which develops color in response to a specific component of a sample.

The stage 3 comprises a guide portion 30 for guiding the movement of a sliding block 50 of the conveying mechanism 5 to be described below, and also comprises a recess 31 for exposing the lower surface of the test tool 7 placed on the stage 3. A prism 42 of the detecting mechanism 4, to be described below, is disposed in the recess 31. The stage 3 is provided with a placement area 32 and a light-measuring area 33. The placement area 32 is an area in which the test tool 7, introduced into the interior of the housing 2 through the introduction portion 22 (see FIG. 1), is placed. The light-measuring area 33 is an area in which a specific component of a sample supplied onto the reagent pad 71 is subjected to light-measurement by the light-measuring mechanism 6.

Figure 3:
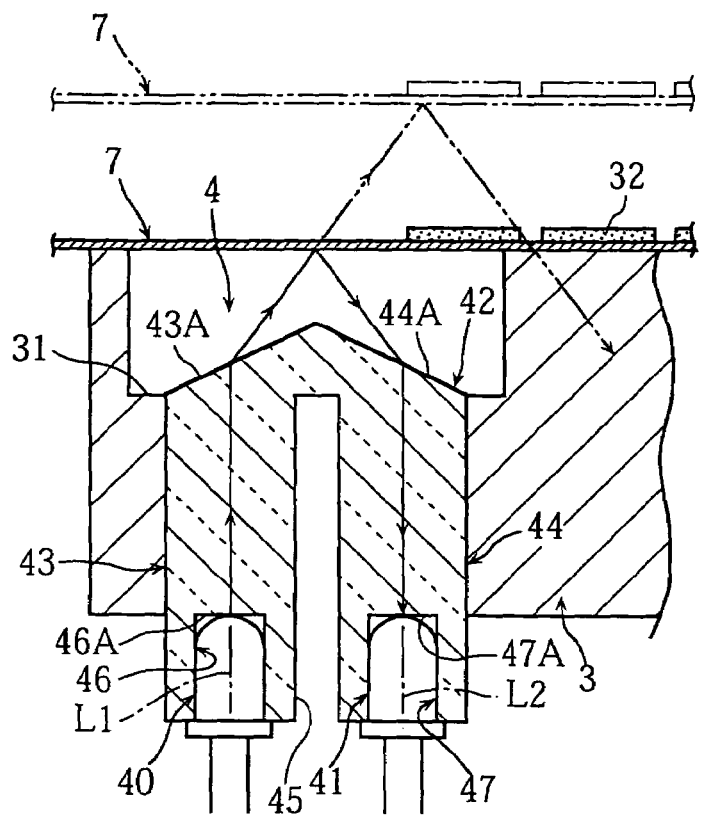
FIG. 3 is a sectional view along a line III-III in FIG. 2.

The detecting mechanism 4 determines whether or not the test tool 7 is placed in the placement area 32, and comprises a light-emitting unit 40, a light-receiving unit 41, and the prism 42 serving as a light guide, as shown in FIG. 3.

The light-emitting unit 40 emits light toward the upper side of the stage 3 such that when the test tool 7 is placed in the placement area 32, the rear surface of the test tool 7 is irradiated with the light. The light-emitting unit 40 is fixed to the prism 42 so that a light emission axis L1 faces the thickness direction (the vertical direction in FIG. 3) of the stage 3. The light-receiving unit 41 receives light traveling from the upper side of the stage 3, and is fixed to the prism 42 so that a light reception axis L2 is parallel or substantially parallel to the light emission axis L1 of the light-emitting unit 40. The light-emitting unit 40 comprises a light-emitting diode, for example, while the light-receiving unit 41 comprises a photodiode, for example. The light-emitting unit 40 and the light-receiving unit 41 need not necessarily be fixed to the prism 42, and the detecting mechanism 4 may be constituted separately from the prism 42.

The prism 42 comprises light-guiding portions 43, 44, and is entirely transparent. The light-guiding portions 43, 44 are separated by a slit 45. The slit 45 is provided to prevent light from the light-emitting unit 40 from being received directly in the light-receiving unit 41.

The light-guiding portion 43 comprises a recess 46 into which the light-emitting unit 40 is fitted and fixed. The bottom surface of the recess 46 constitutes an entrance surface 46A for introducing light from the light-emitting unit 40 into the interior of the light-guiding portion 43. The entrance surface 46A is orthogonal to the light emission axis L1. The light-guiding portion 43 also comprises an output surface 43A for outputting light from the interior of the light-guiding portion 43 toward the upper side of the stage 3. The output surface 43A is formed as an inclined plane in relation to the light emission axis L1 (light reception axis L2), and serves to refract light passing through the output surface 43A.

Meanwhile, the light-guiding portion 44 comprises an entrance surface 44A for introducing reflection light from the test tool 7 into the interior of the light-guiding portion 44. The entrance surface 44A is formed as a plane having an opposite incline to the output surface 43A in relation to the light reception axis L2 (light emission axis L1), and serves to refract light passing through the entrance surface 44A. More specifically, of the light emitted toward the upper side of the stage 3 from the output surface 43A, the entrance surface 44A conducts regular reflection light from the test tool 7, placed in the placement area 32 of the stage 3, through the interior of the light-guiding portion 44 along the light reception axis L2. The light-guiding portion 44 also comprises a recess 47 into which the light-receiving unit 41 is fitted and fixed. The bottom surface of the recess 47 constitutes an output surface 47A for outputting light from the interior of the light-guiding portion 44 toward the light-receiving unit 41. The output surface 47A is orthogonal to the light reception axis L2.

In the detecting mechanism 4, light emitted from the light-emitting unit 40 is introduced into the light-guiding portion 43 through the entrance surface 46A, travels along the light emission axis L1, and is then outputted from the light-guiding portion 43 toward the upper side of the stage 3 through the output surface 43A. When the test tool 7 is not present in the placement area 32 of the stage 3, the light outputted from the light-guiding portion 43 is not received in the light-receiving unit 41. In contrast, when the test tool 7 is placed in the placement area 32, the rear surface of the test tool 7 is irradiated with the light output from the light-guiding portion 43, and the resulting reflection light enters the entrance surface 44A of the light-guiding portion 44. Of the light entering the entrance surface 44A, light that is reflected regularly on the rear surface of the test tool 7 is selectively introduced into the light-guiding portion 44. The light introduced into the light-guiding portion 44 travels along the light reception axis L2, and is then outputted from the output surface 47A and received in the light-receiving unit 41.

Thus, in the detecting mechanism 4, regular reflection light produced when the test tool 7 is placed in the placement area 32 is actively introduced into the light-guiding portion 44 of the prism 42 and received in the light-receiving unit 41. Accordingly, when the test tool 7 is not placed in the placement area 32, for example when the test tool 7 is positioned above the placement area 32 as shown by the virtual lines in FIG. 3, the resulting regular reflection light is not introduced into the prism 42. As a result, the situations, in which the detecting mechanism 4 mistakenly detects the presence of the test tool 7 even though the test tool 7 is not placed in the placement area 32, can be suppressed.

Figure 4:
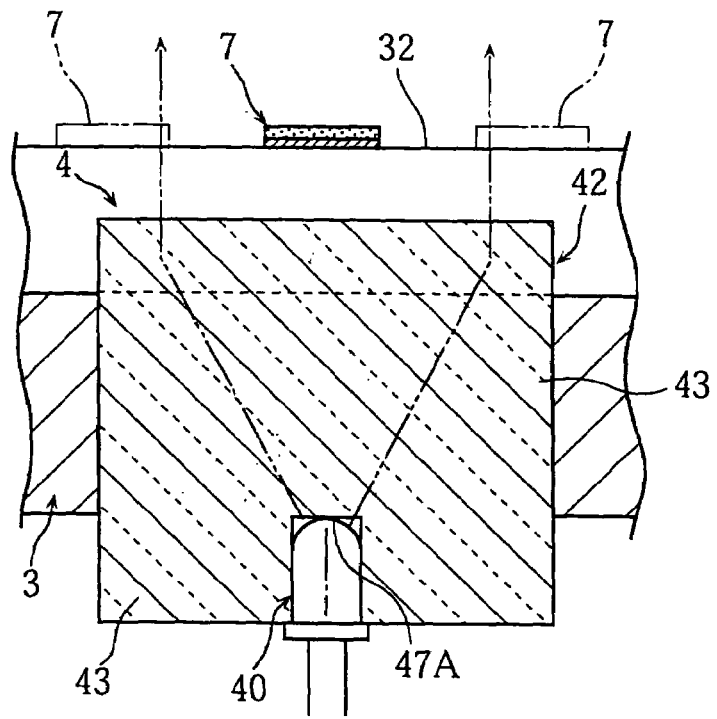
FIG. 4 is a sectional view along a line IV-IV in FIG. 2.

A light-emitting diode has lower directivity than a laser diode. Therefore, by employing a light-emitting diode as the light-emitting unit 40 of the detecting mechanism 4, light from the light-emitting unit 40 widens when outputted from the light-guiding portion 43, as shown in FIG. 4. Hence, by employing a light-emitting diode as the light-emitting unit 40, light can be emitted in a comparatively wide range, enabling an increase in the range in which the presence of the test tool 7 can be detected. As a result, the test tool 7 can be detected even when a user places the test tool 7 manually such that the test tool 7 is not positioned with exactitude, thereby lessening the burden on the user when placing the test tool 7.

In the detecting mechanism 4, the light-emitting unit 40 and light-receiving unit 41 are disposed such that the light emission axis L1 and light reception axis L2 are parallel to each other. In so doing, the distance between the light-emitting unit 40 and light-receiving unit 41 can be reduced in comparison with a constitution in which the light-emitting unit and light-receiving unit are disposed such that the light emission axis and light reception axis are not parallel to each other. As a result, a reduction in the size of the detecting mechanism 4, and a corresponding reduction in the size of the analyzing device 1, can be achieved.

Figure 5:
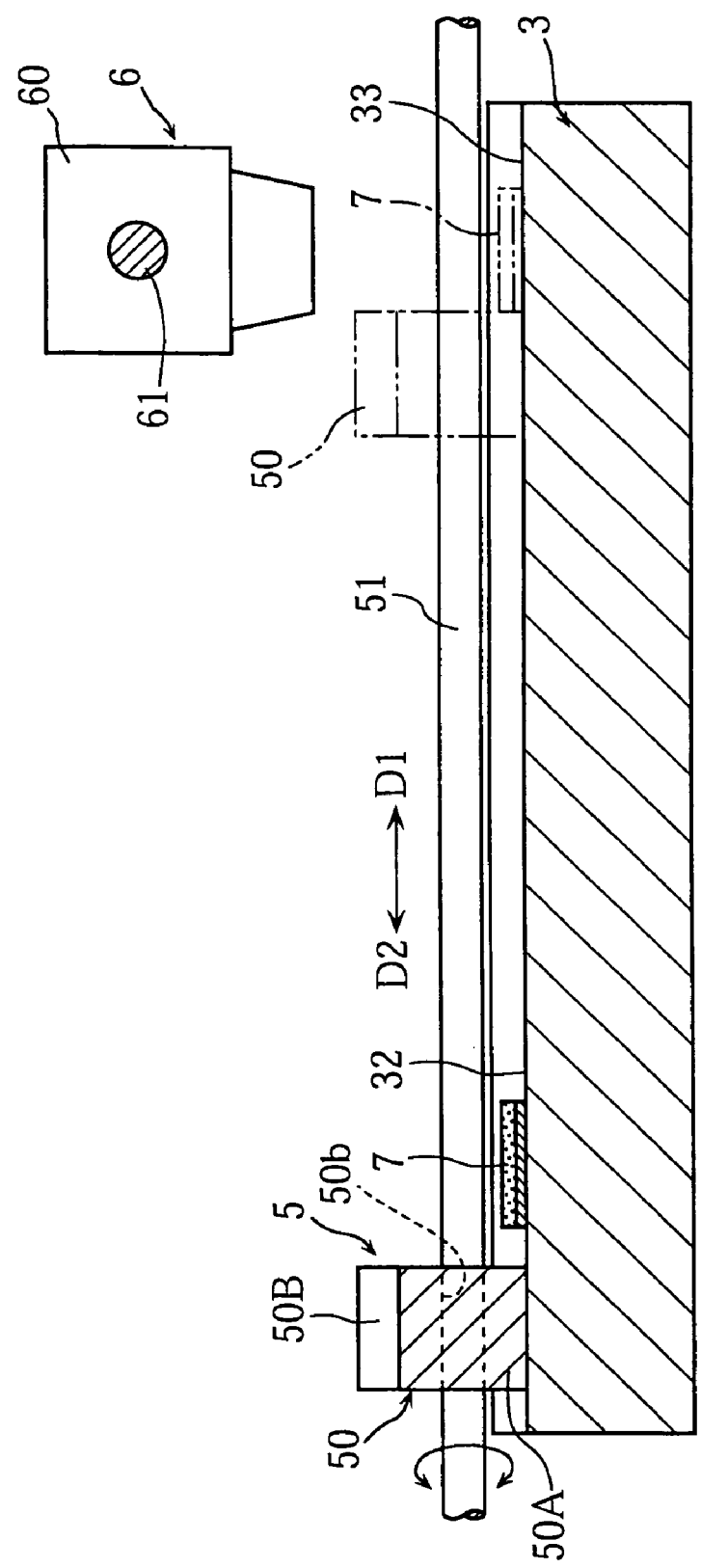
FIG. 5 is a sectional view along a line V-V in FIG. 2.

As shown in FIGS. 2 and 5, the conveying mechanism 5 serves to move the test tool 7 from the placement area 32 to the light-measuring area 33 of the stage 3. The conveying mechanism 5 comprises the sliding block 50, which is capable of a reciprocating motion over the upper surface of the stage 3 in a direction indicated by arrows D1, D2 in the drawings, and a guiding rod 51 for causing the sliding block 50 to perform this reciprocating motion. The sliding block 50 comprises an interfering portion 50A which slides over the upper surface of the stage 3, and a connecting portion 50B connected to the guiding rod 51 so as to be capable of moving relative thereto. A throughhole 50b formed with a thread groove (not shown) on its inner surface is provided in the connecting portion 50B. A thread ridge (not shown) is formed on the surface of the guiding rod 51, and hence the guiding rod 51 is screwed to the sliding block 50 via the through hole 50b. Thus, by rotating the guiding rod 51, the sliding block 50 can be moved according to the rotational direction of the guiding rod 51. The guiding rod 51 is rotated, for example, by linking the guiding rod 51 to a power source such as a motor, not shown in the drawing, and using the output of the power source. By rotating the guiding rod 51 in a predetermined direction such that the sliding block 50 is moved in the direction of the arrow D1 in the drawings, the test tool 7 can be moved from the placement area 32 to the light-measuring area 33.

Figure 6:
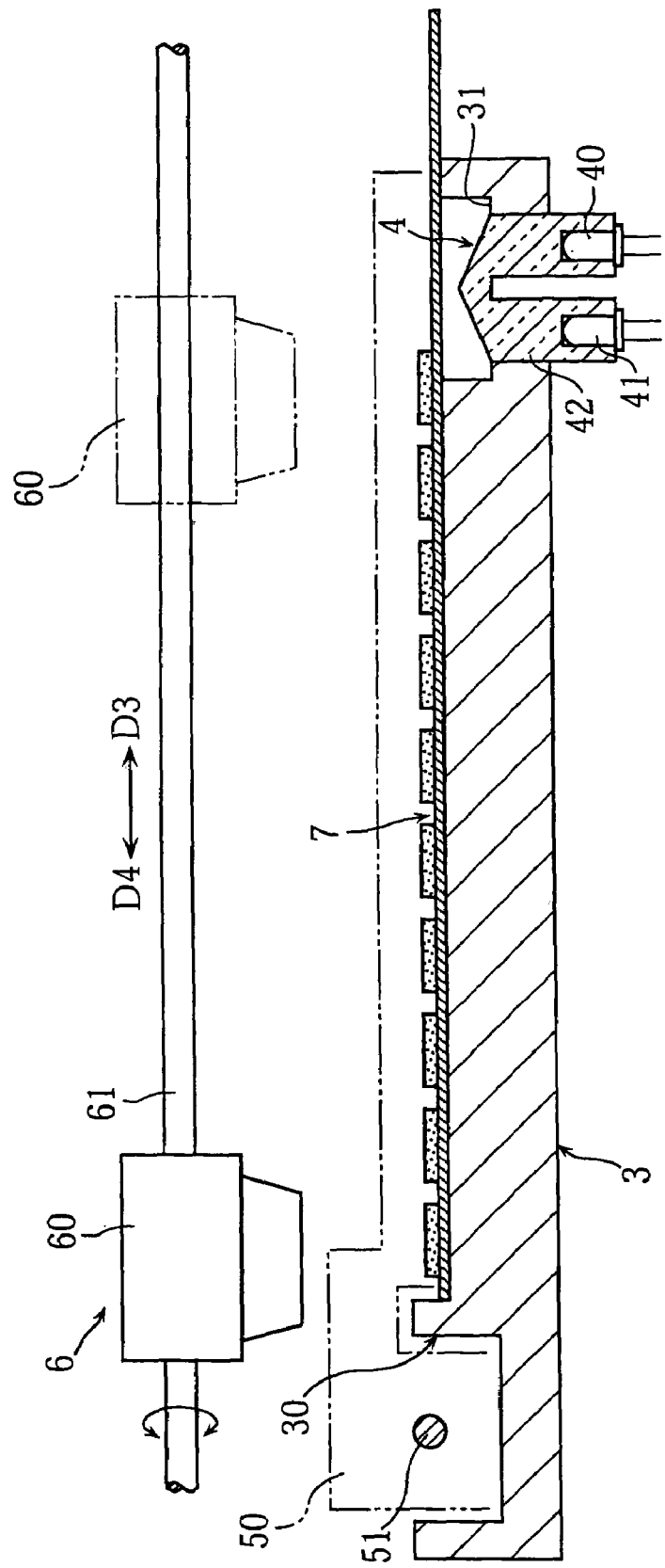
FIG. 6 is a sectional view along a line VI-VI in FIG. 2.
Figure 7:
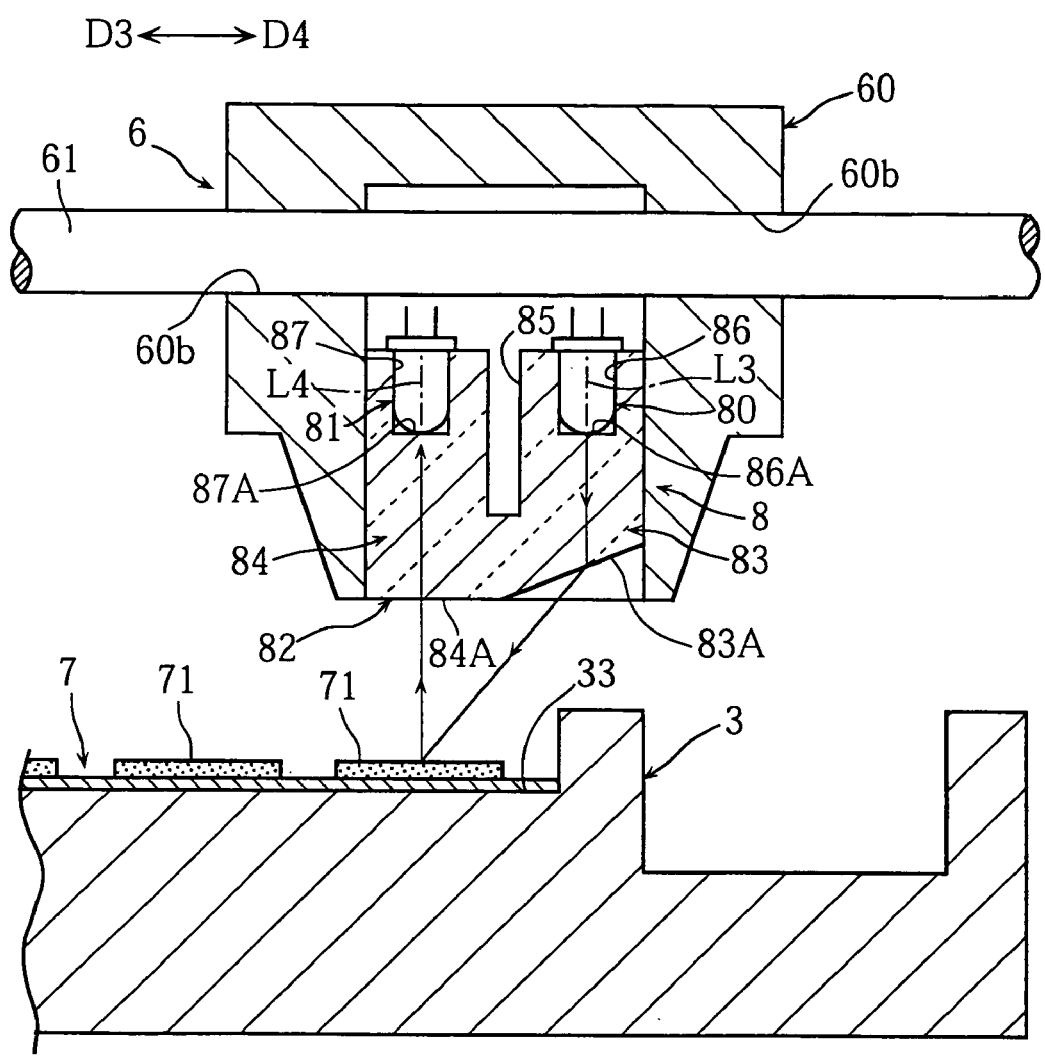
FIG. 7 is a sectional view along a line VII-VII in FIG. 2.

As shown in FIGS. 2, 6, and 7, the light-measuring mechanism 6 optically measures the degree of coloration of the reagent pads 71 on the test tool 7. The light-measuring mechanism 6 comprises a slider 60 capable of a reciprocating motion along the surface of the stage 3 in a direction indicated by arrows D3, D4 in the drawings, a guiding rod 61 for causing the slider 60 to perform this reciprocating motion, and the light sensor 8 carried on the slider 60.

The slider 60 comprises a through hole 60b formed with a thread groove (not shown) on its inner surface. A thread ridge (not shown) is formed on the surface of the guiding rod 61, and hence the guiding rod 61 is screwed to the slider 60 via the through hole 60b. Thus, by rotating the guiding rod 61, the slider 60, and accordingly the light sensor 8, can be moved in the direction of the arrows D3, D4 in the drawings in accordance with the rotational direction of the guiding rod 61. The guiding rod 61 is rotated, for example, by linking the guiding rod 61 to a power source such as a motor, not shown in the drawing, and using the output of the power source.

Figure 8:
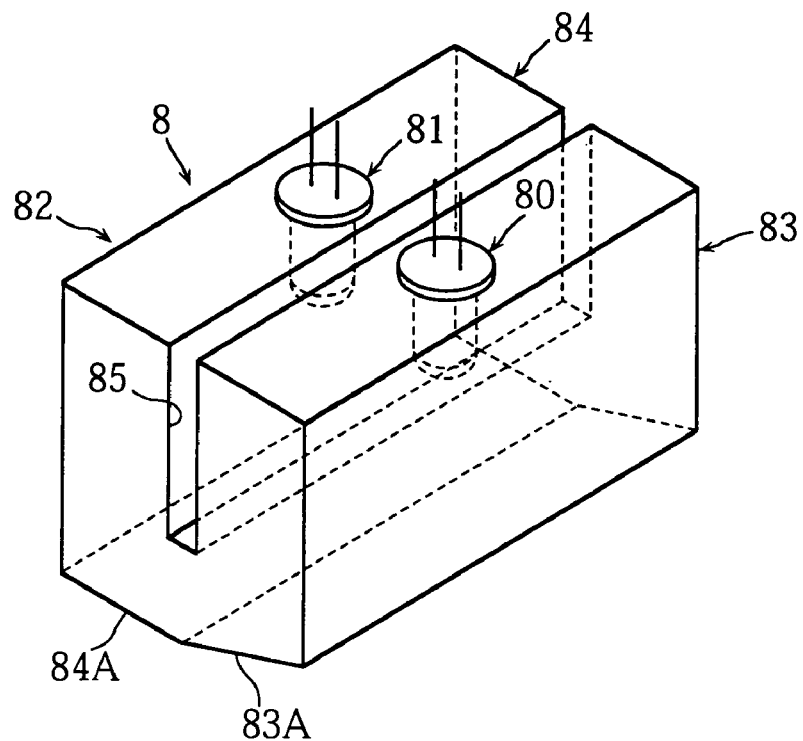
FIG. 8 is a perspective view showing the main parts of a light-measuring mechanism.

As shown in FIGS. 7 and 8, the light sensor 8 comprises a light-emitting unit 80, a light-receiving unit 81, and a prism 82.

The light-emitting unit 80 emits light toward the stage 3, and is fixed to the prism 82 such that a light emission axis L3 extends in the thickness direction (the vertical direction in FIG. 7) of the stage 3. The light-receiving unit 81 receives light traveling from the stage 3, and is fixed to the prism 82 such that a light reception axis L4 is parallel or substantially parallel to the light emission axis L3 of the light-emitting unit 80. The light-emitting unit 80 comprises a light-emitting diode, for example, while the light-receiving unit 81 comprises a photodiode, for example.

The prism 82 comprises a light-guiding portion 83 and a light-guiding portion 84, and is entirely transparent. These areas 83, 84 are separated by a slit 85. The slit 85 is provided to prevent light from the light-emitting unit 80 from being received directly in the light-receiving unit 81.

The light-guiding portion 83 comprises a recess 86 into which the light-emitting unit 80 is fitted and fixed. The bottom surface of the recess 86 constitutes an entrance surface 86A for introducing light from the light-emitting unit 80 into the interior of the light-guiding portion 83. The entrance surface 86A is orthogonal to the light emission axis L3. The light-guiding portion 83 also comprises an output surface 83A for outputting light from the interior of the light-guiding portion 83 toward the test tool 7. The output surface 83A is formed as an inclined plane in relation to the light emission axis L3 (light reception axis L4), and serves to refract light passing through the output surface 83A.

Meanwhile, the light-guiding portion 84 comprises an entrance surface 84A for introducing light from the test tool 7 into the interior of the light-guiding portion 84. The entrance surface 84A is orthogonal to the light reception axis L4 (light emission axis L3). More specifically, of the light emitted toward the test tool 7 from the output surface 83A, the entrance surface 84A conducts scattered light from the test tool 7, traveling along the light reception axis L4, through the interior of the light-guiding portion 84 along the light reception axis L4 without refracting the light. The light-guiding portion 84 also comprises a recess 87 into which the light-receiving unit 81 is fitted and fixed. The bottom surface of the recess 87 constitutes an output surface 87A for outputting light from the interior of the light-guiding portion 84 toward the light-receiving unit 81. The output surface 87A is orthogonal to the light reception axis L4.

The light sensor 8 is moved in the direction of the arrows D3, D4 in the drawing (the length direction of the test tool 7) together with the slider 60 by rotating the guiding rod 61. Hence in the light-measuring mechanism 6, by emitting light from the light-emitting unit 80 while moving the light sensor 8 in the length direction of the test tool 7, all of the plurality of reagent pads 71 can be irradiated with light. At the same time, the scattered light from each reagent pad 71 can be received in the light-receiving unit 81.

Figure 9:
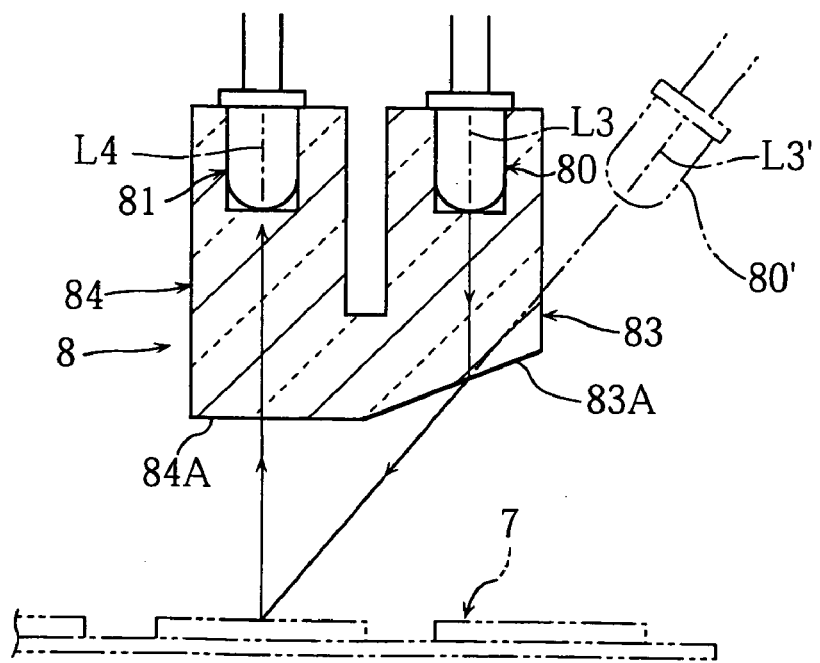
FIG. 9 is a sectional view illustrating the workings of the light-measuring mechanism.

In the light-measuring mechanism 6 (light sensor 8) described above, the light-emitting unit 80 and light-receiving unit 81 are disposed such that the light emission axis L3 and light reception axis L4 are parallel to each other. In so doing, the distance between the light-emitting unit 80 and light-receiving unit 81 in the light sensor 8 can be reduced in comparison with a constitution in which a light-emitting unit 80' and the light-receiving unit 81 are disposed such that a light emission axis L3' and the light reception axis L4 are not parallel to each other, as shown by the virtual lines in FIG. 9. As a result, a reduction in the size of the light sensor 8, and a corresponding reduction in the size of the light-measuring mechanism 6 and the analyzing device 1, can be achieved.

In the illustrated light sensor 8, the output surface 83A is inclined in relation to the light emission axis L3 (light reception axis L4), while the entrance surface 84A is orthogonal to the light reception axis L4 (light emission axis L3). However, the output surface may be orthogonal to the light emission axis L3 (light reception axis L4) and the entrance surface 84A inclined in relation to the light reception axis L4 (light emission axis L3), or both the output surface and entrance surface may be inclined in relation to the light emission axis L3 and light reception axis L4.

The present invention is not limited to the embodiment described above. For example, constitutions such as those shown in FIGS. 10A to 10E may be employed as a detecting mechanism, and constitutions such as those shown in FIGS. 11 to 16 may be employed as a light sensor.

In a detecting mechanism 4A shown in FIG. 10A, the light guide is constituted as a prism 42A, where the prism 42A corresponds in arrangement to the prism 42 of the detecting mechanism 4 (see FIG. 3, for example) turned upside down.

In a detecting mechanism 4B shown in FIG. 10B, the light guide is constituted as a cylindrical lens 42B.

In a detecting mechanism 4C shown in FIG. 10C, the light guide is constituted as a Fresnel lens 42C. The Fresnel lens 42C comprises a plurality of protruding portions 42Ca such that its upper surface is irregular. The detecting mechanism 4C also comprises a cover 42Cb covering the protruding portions 42Ca. Thus the upper surface of the detecting mechanism 4C is made planar.

In a detecting mechanism 4D shown in FIG. 10D, a cover 42Db is formed integrally with the upper surface (irregular surface) of a Fresnel lens 42D. The upper surface of this detecting mechanism 4D is also planar.

In the detecting mechanisms 4C, 4D shown in FIGS. 10C and 10D, the upper surface of the light guide is planar, and therefore the height dimension of a central portion can be reduced in comparison with a case in which the upper surface is pointed or curved (see FIGS. 3, 10A, and 10B). Thus, with the detecting mechanisms 4C, 4D, the dimensions of the detecting mechanisms 4C, 4D can be reduced. Furthermore, by covering the upper surface of the Fresnel lenses 42C, 42D with the covers 42Cb, 42Db, dust or dirt can be prevented from adhering to the upper surface of the Fresnel lenses 42C, 42D. Moreover, since the dust or dirt adheres to the covers 42Cb, 42Db, which have fewer irregularities than the Fresnel lenses 42C, 42D, the dust and dirt can be removed easily.

In a detecting mechanism 4E shown in FIG. 10E, the light guide is constituted as a lens 42E combining a cylindrical lens and a Fresnel lens. In the detecting mechanism 4E also, the upper surface of the lens 42E may be covered with a cover.

Figure 11:
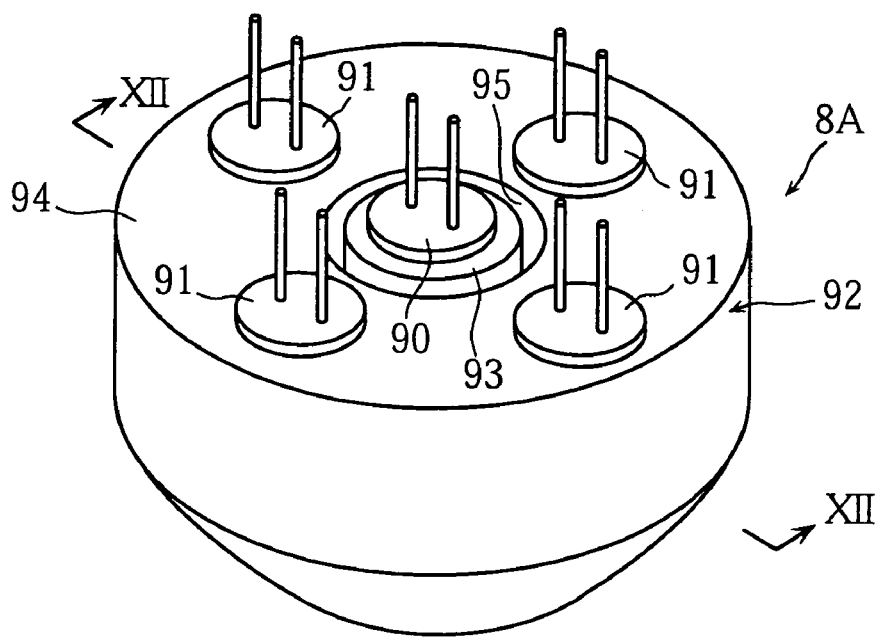
FIG. 11 is a perspective view showing another example of a light sensor in the light-measuring mechanism.
Figure 12:
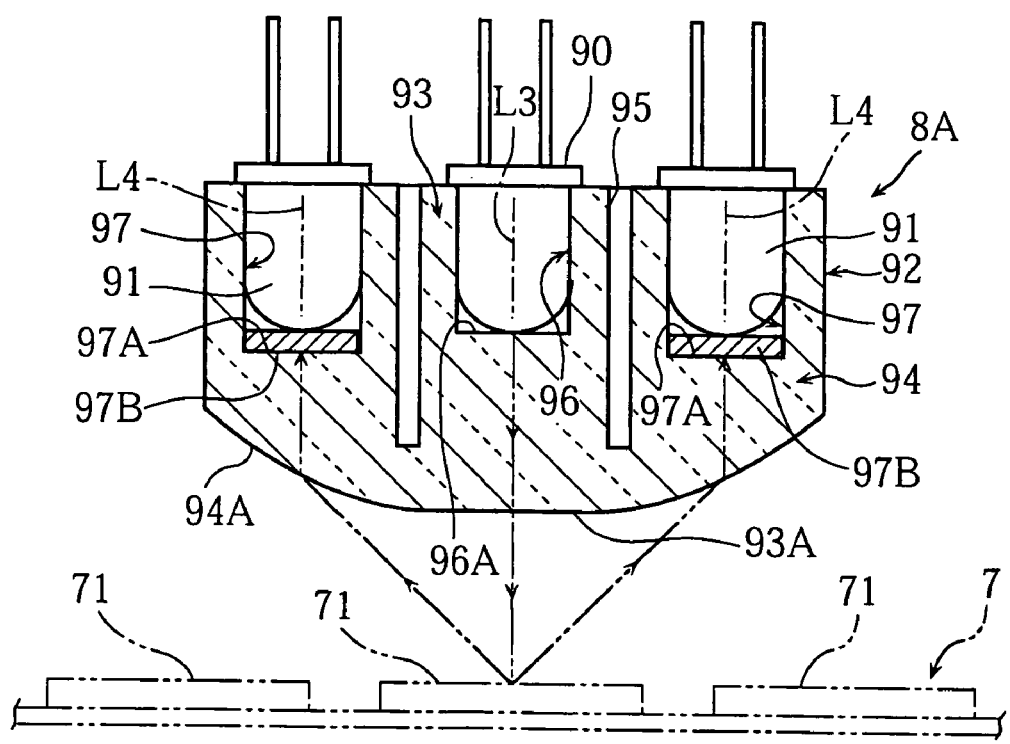
FIG. 12 is a sectional view along a line XII-XII in FIG. 11.

A light sensor 8A shown in FIGS. 11 and 12 comprises a single light-emitting unit 90, four light-receiving units 91, and a light guide 92 formed in a transparent columnar form. The light guide 92 is formed with an annular recess 95. This recess 95 divides the light guide 92 into a light-guiding portion 93 and a light-guiding portion 94.

The light-guiding portion 93 takes a columnar form, and comprises a recess 96 to which the light-emitting unit 90 is fixed. The light-emitting unit 90 comprises a white LED, for example. A bottom surface 96A of the recess 96 constitutes an entrance surface for introducing light emitted from the light-emitting unit 90 into the light-guiding portion 93. The entrance surface 96A is orthogonal to the light emission axis L3 of the light-emitting unit 90. The light-guiding portion 93 also comprises an output surface 93A for outputting light from the interior of the light-guiding portion 93 to the outside. The output surface 93A is constituted as a plane that is orthogonal to the light emission axis L3 (parallel to the entrance surface 96A).

The light-guiding portion 94 takes an annular form, and comprises an entrance surface 94A which is inclined in relation to the light reception axes L4 of the light-receiving units 91. The entrance surface 94A is constituted as a curved surface. The light-guiding portion 94 comprises four recesses 97 to which the light-receiving units 91 are fixed. The recesses 97 are provided concentrically so as to surround the recess 96 of the light-guiding portion 93. Thus the four light-receiving units 91 are disposed so as to surround the light-emitting unit 90, and such that the light reception axes L4 thereof are parallel to the light emission axis L3 of the light-emitting unit 90. A bottom surface 97A of each recess 97 constitutes an output surface for introducing light into the light-receiving units 91. A wavelength selection portion 97B is provided on the bottom portion of each recess 97. The four wavelength selection portions 97B each transmit light of different wavelengths. Accordingly, light of different wavelengths is selected in each light-receiving unit 91. The wavelength selection portions 97B are constituted by interference filters or color filters, for example.

In the light sensor 8A, of the light that is emitted from the light-emitting unit 90 and reflected on the reagent pads 71, light of different wavelengths is received in each light-receiving unit 91. Hence, even when the test tool 7 is constituted to measure a plurality of analysis items corresponding to different measurement wavelengths, appropriate measurement can be performed by setting the wavelength to be selected by the wavelength selection portions 97B.

In the light sensor 8A, the light emission axis L3 of the light-emitting unit 90 and the light reception axis L4 of each light-receiving unit 91 are disposed parallel to each other. In so doing, in the light sensor 8A, the size of the light sensor 8A, and accordingly the size of the light-measuring mechanism, can be reduced in a similar manner to the light sensor 8 (see FIGS. 7 through 9) described above.

Figure 13A:
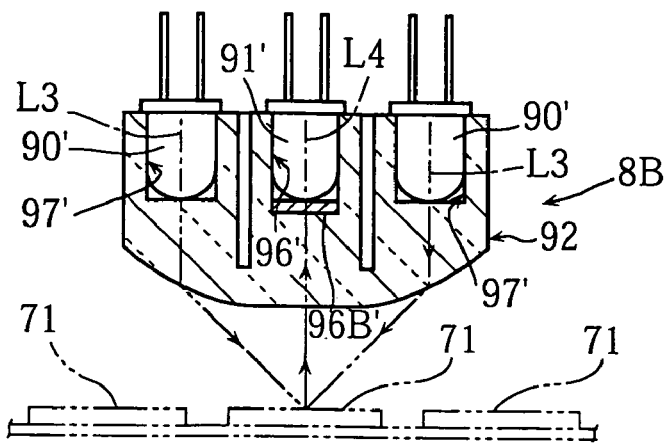
FIGS. 13A to 13C are sectional views showing further examples of the light sensor in the light-measuring mechanism.

A light sensor 8B shown in FIG. 13A comprises four light-emitting units 90' and a single light-receiving unit 91' such that the arrangement of the light-emitting unit and light-receiving units in the light sensor 8A (see FIGS. 11 and 12) is switched. More specifically, the light-receiving unit 91' is disposed in the central portion of the light guide 92, and the four light-emitting units 90' are disposed so as to surround the light-receiving unit 91'. The light-emitting units 90' and light-receiving unit 91' are disposed so that the light emission axis L3 of each light-emitting unit 90' is parallel to the light reception axis L4 of the light-receiving unit 91'. A wavelength selection portion 96B' is provided on the bottom portion of a recess 96' to which the light-receiving unit 91' is fixed. Accordingly, only light of a specific wavelength enters the light-receiving unit 91'. It should be noted that the wavelength selection portion 96B' may be omitted.

In the light sensor 8B, the reagent pads 71 are irradiated with light from the four light-emitting units 90', and reflection light from the reagent pads 71 is received in the single light-receiving unit 91'. Therefore, in the light sensor 8B, the quantity of light emitted onto the reagent pads 71 can be increased, thus securing a larger quantity of reception light in the light-receiving unit 91'. As a result, even when light measurement is performed on the basis of scattered light, which tends to produce a small quantity of reception light, for example, the light can be measured appropriately.

In the light sensor 8B, wavelength selection portions may be provided on recesses 97' to which the light-emitting units 90' are fixed such that the wavelength of light entering the light guide 92 from each recess 97' is selected. In this case, each wavelength selection portion may be constituted to transmit light of the same wavelength or light of a different wavelength, depending on the constitution of the test tool 7.

Figure 13B:
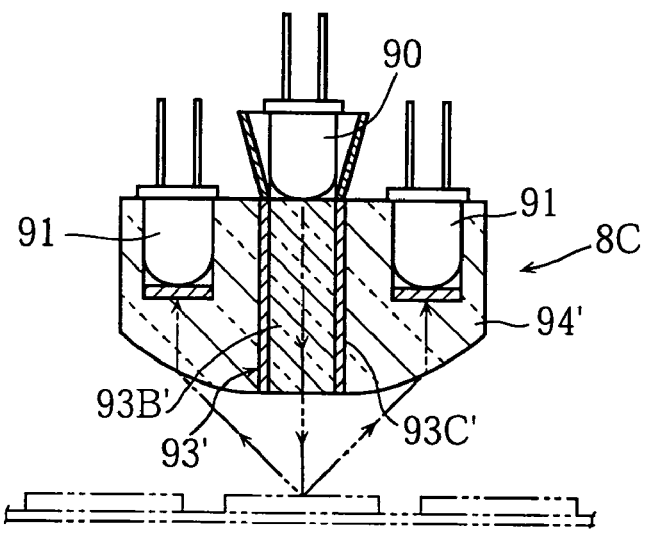

In a light sensor 8C shown in FIG. 13B, the output light-guiding portion of the light sensor 8A (see FIGS. 11 and 12) is constituted by an optical fiber 93'. The optical fiber 93' comprises a core portion 93B' formed transparently, and a cladding portion 93C' surrounding the core portion 93B' and having a smaller refractive index than the core portion 93B'. The optical fiber 93' is surrounded by an outer shell portion 94'.

With the light sensor 8C, the reagent pads 71 can be irradiated efficiently with light from the light-emitting unit 90 due to the action of the optical fiber 93'. As a result, the quantity of light received in the light-receiving unit 91 can be increased.

Figure 13C:
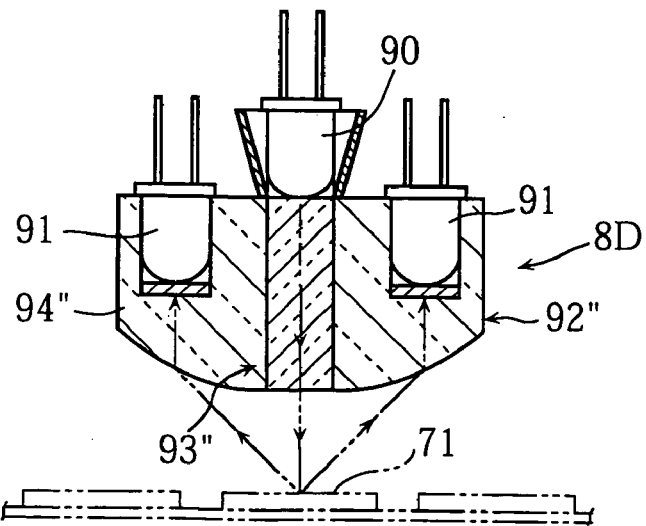

Similarly to the light sensor 8C (see FIG. 13B), in a light sensor 8D shown in FIG. 13C, a light guide 92" is constituted by a core portion 93" and an outer shell portion 94" surrounding the core portion 93". However, in the light sensor 8D, the core portion 93" has a higher refractive index than the outer shell portion 94", the outer shell portion 94" functions as a cladding layer, and the entire light guide 92" constitute an optical fiber. In the light sensor 8D also, the reagent pads 71 can be irradiated efficiently with light from the light-emitting unit 90, and therefore the quantity of light received in the light-receiving unit 91 can be increased.

Figure 14A:
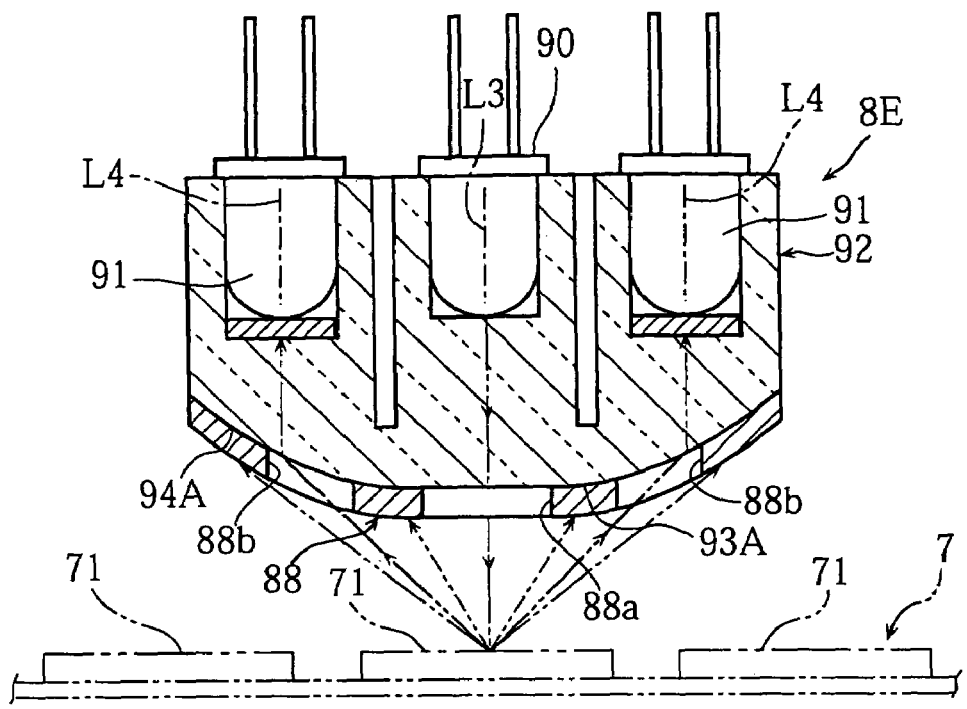
FIG. 14A is a sectional view showing a further example of the light sensor in the light-measuring mechanism.

In a light sensor 8E shown in FIG. 14A, a light-shielding mask 88 is deposited so as to cover the output surface 93A and entrance surface 94A of the light guide 92 in the light sensor 8A shown in FIGS. 11 and 12. Of the light reflected on the reagent pads 71 of the test tool 7, the light-shielding mask 88 causes light reflected on the reagent pads 71 at an angle of 45 degrees or substantially 45 degrees to enter the light guide 92, and accordingly the light-receiving units 91. The entire light-shielding mask 88 is formed from a material which absorbs light easily, and as shown in FIG. 14B, is formed with five through holes 88a, 88b corresponding to the sum total of the light-emitting unit 90 and light-receiving units 91.

Figure 14B:
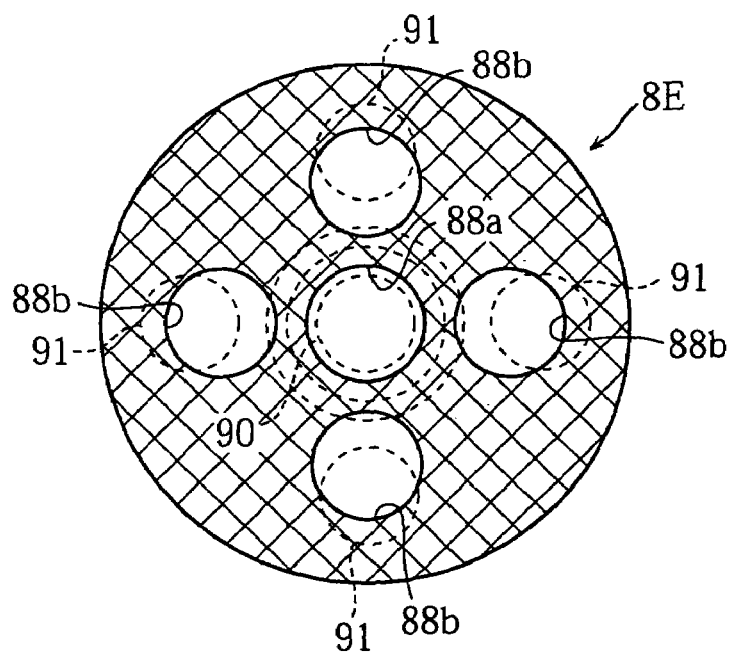
FIG. 14B is a bottom view of the light sensor shown in FIG. 14A.

In FIG. 14B, the part shaded in cross hatching denotes the light-shielding mask 88. The through hole 88a transmits light emitted from the light-emitting unit 90 and output from the light guide 92, whereas the through holes 88b transmit light reflected by the reagent pads 71 toward the light guide 92. This type of light-shielding mask 88 may be formed by vapor deposition or printing using a black resin material, for example.

In the light sensor 8E, of the light that is reflected on the reagent pads 71, only light reflected at an angle of 45 degrees or substantially 45 degrees is received in the light-receiving unit 91, and the remaining light is absorbed by the light-shielding mask 88. Hence, target reflection light required for light measurement can be caused to enter the light-receiving units 91 selectively, and therefore, if the light sensor 8E is used, the analysis precision is improved.

Figure 15A:
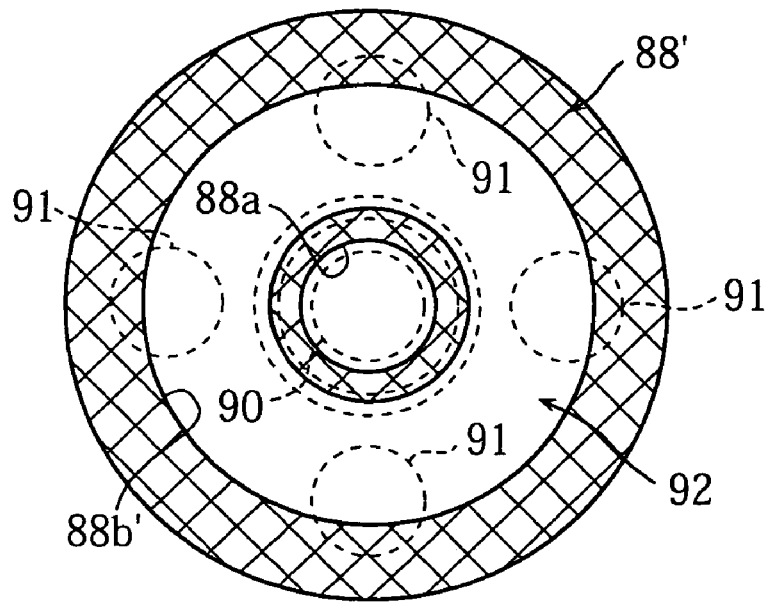
FIGS. 15A and 15B are bottom views showing further examples of the light sensor in the light-measuring mechanism.
Figure 15B:
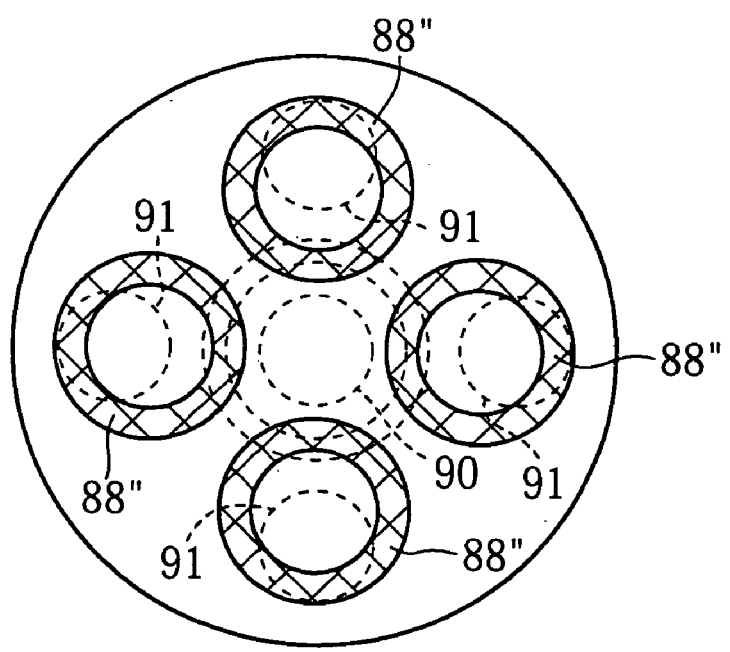

The light-shielding means may take the forms shown in FIGS. 15A and 15B. In a light-shielding mask 88' shown in FIG. 15A, a through hole 88b' is formed in annular form for transmitting light that is reflected by the reagent pads 71 (see FIG. 14A) toward the light guide 92. In other words, the light entering all of the light-receiving units 91 is restricted by the single through hole 88b'. In contrast, the light-shielding means shown in FIG. 15B comprise four annular light-shielding masks 88" provided individually for each light-receiving unit 91.

Figure 16:
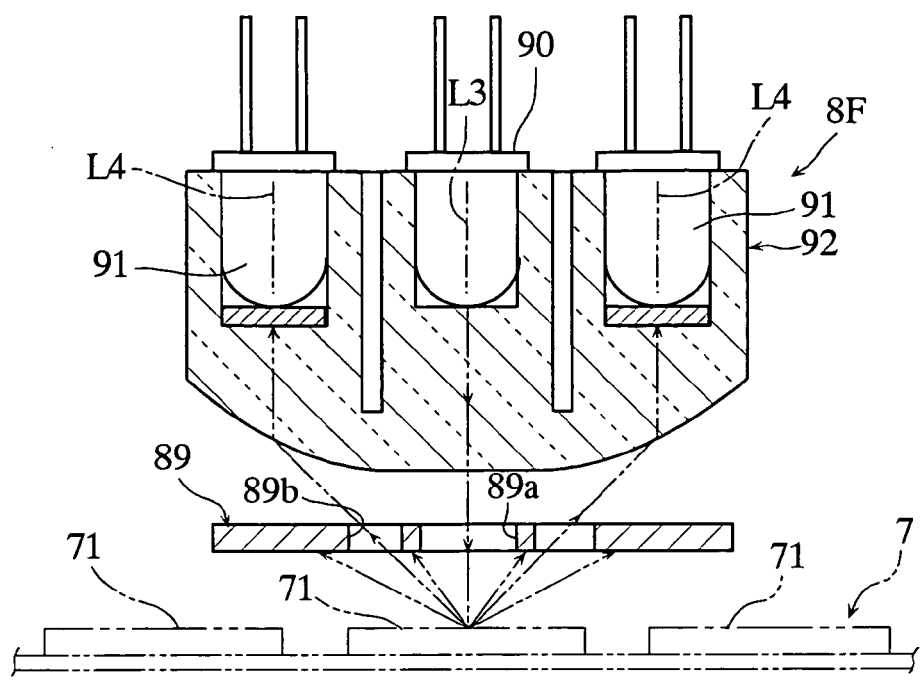
FIG. 16 is a sectional view of a light sensor illustrating another example of light-shielding means.
Figure 17:
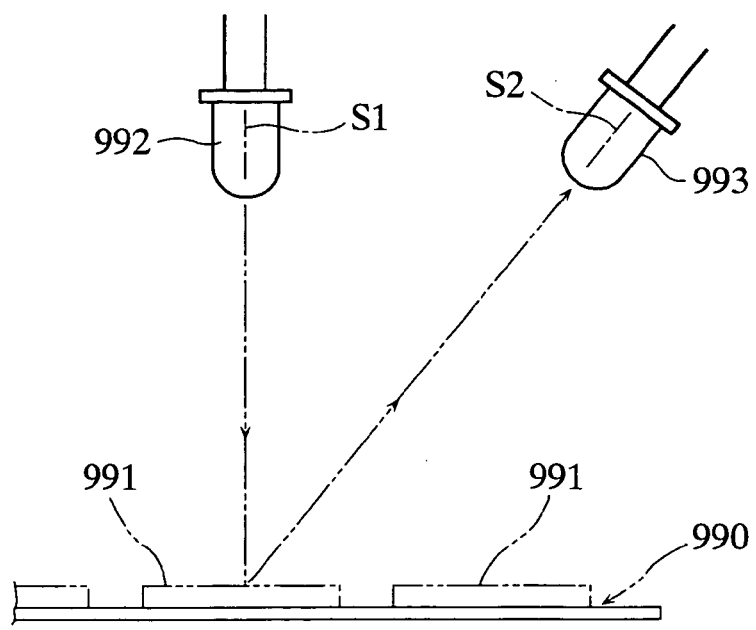
FIG. 17 is a schematic view illustrating an example of a conventional light-measuring mechanism.
Figure 18:
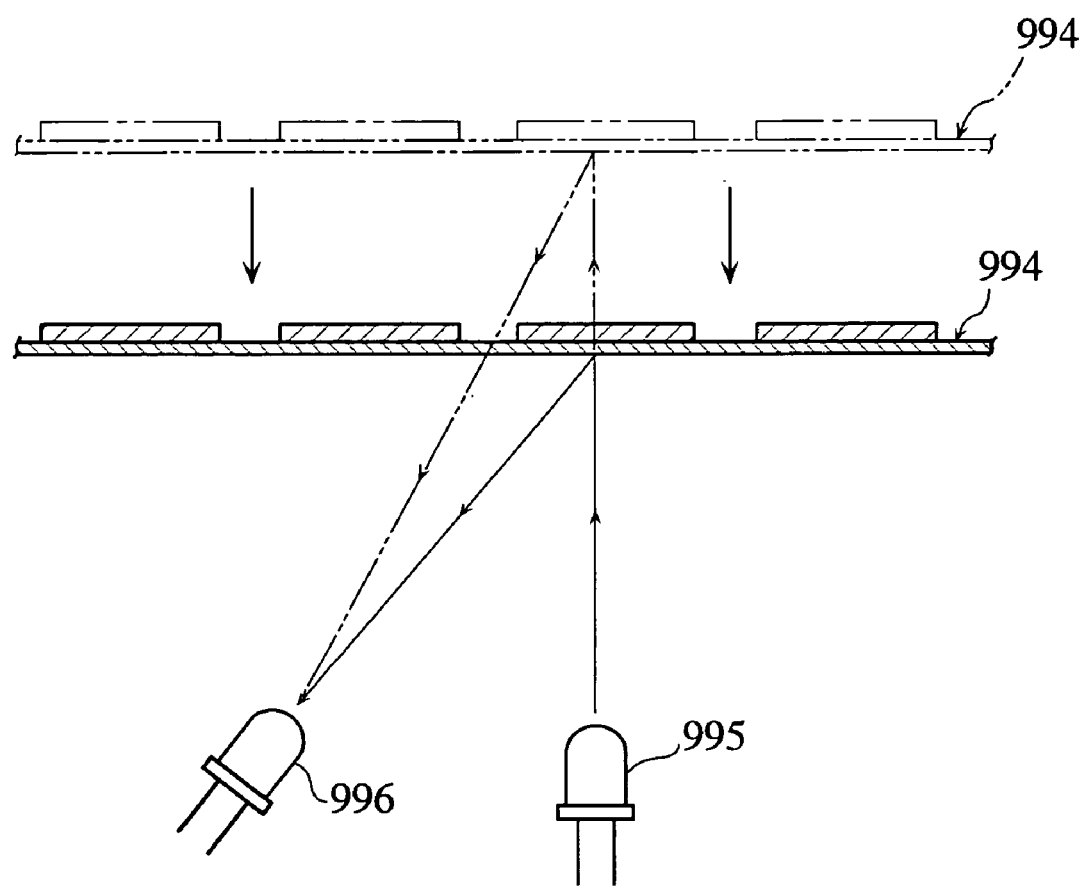
FIG. 18 is a schematic view illustrating an example of conventional detecting means for detecting a test tool.

In a light sensor 8F shown in FIG. 16, a light shield 89 is provided separately from the light guide 92 and disposed at a remove from the light guide 92. Although not shown clearly in the drawing, the light shield 89 is formed with through holes 89a, 89b in a similar arrangement to the light-shielding masks 88, 88' shown in FIGS. 14B and 15A. When the light shield 89 is constituted separately from the light guide 92, the light shield 89 is fixed to the slider 60 (see FIG. 7), for example, so as to move together with the light guide 92.

The light-shielding masks 88, 88', 88" and the light shield 89, described with reference to FIGS. 14 through 16, are examples, and the form thereof may be modified in various ways as long as the target reflection light can be received selectively in the light-receiving unit. Moreover, the light shield may be employed not only in the light sensors shown in FIGS. 11 and 12, but also in the other light sensors.

The invention claimed is:

1. An analyzing device comprising:
   a detecting mechanism for detecting whether or not a test tool exists in a placement area, the detecting mechanism including a detection light-emitting unit for emitting light onto the test tool and a detection light-receiving unit for receiving reflection light from the test tool;
   a conveying mechanism for transferring the test tool from the placement area to a light-measuring area which is different from the placement area;
   a light-measuring mechanism including a measurement light-emitting unit for emitting light onto the test tool transferred to the light-measuring area, and a measurement light-receiving unit for receiving reflection light from the test tool; and
   wherein a light emission axis of the detection light-emitting unit and a light reception axis of the detection light-receiving unit are parallel or substantially parallel to each other.

2. The analyzing device according to claim 1, wherein a light emission axis of the measurement light-emitting unit and a light reception axis of the measurement light-receiving unit are parallel or substantially parallel to each other.

3. The analyzing device according to claim 2, further comprising a measurement light guide for defining a path of at least one of light traveling toward the test tool from the measurement light-emitting unit and light traveling toward the measurement light-receiving unit from the test tool.

4. The analyzing device according to claim 3,
   wherein the measurement light guide comprises: a first entrance area for introducing light emitted from the measurement light-emitting unit into the measurement light guide; a first output area for outputting the light introduced into the measurement light guide toward the test tool; a second entrance area for introducing reflection light from the test tool into the measurement light guide; and a second output area for outputting the light reflected by the test tool and then introduced into the light guide toward the measurement light-receiving unit; and wherein at least one of the first entrance area, the first output areas, the second entrance area and the second output area refracts light passing therethrough.

5. The analyzing device according to claim 4, wherein the first output area and the second entrance area are constituted as planar surfaces that are orthogonal or substantially orthogonal to the light emission axis of the measurement light-emitting unit.

6. The analyzing device according to claim 3, wherein the measurement light guide comprises a prism or a lens.

7. The analyzing device according to claim 6, wherein the prism or lens serving as the measurement light guide is formed with recesses for fixedly fitting the detection light-emitting unit and the measurement light-receiving unit, respectively, the prism or lens being further formed with a slit for preventing light from directly entering from the measurement light-emitting unit into the measurement light-receiving unit.

8. The analyzing device according to claim 3, wherein the measurement light guide comprises a core portion extending along the light emission axis of the measurement light emitting unit, and an outer shell portion having a lower refractive index than the core portion and surrounding the core portion.

9. The analyzing device according to claim 8, wherein the outer shell portion functions as a cladding layer, and wherein the measurement light guide as a whole constitutes an optical fiber.

10. The analyzing device according to claim 3, wherein the measurement light guide comprises an optical fiber portion extending along the light emission axis of the measurement light-emitting unit, and an outer shell portion surrounding the optical fiber portion.

11. The analyzing device according to claim 3, further comprising a light shield for causing light reflected by the test tool at a target angle to enter the measurement light-receiving unit selectively.

12. The analyzing device according to claim 11, wherein the target angle is 45 degrees or substantially 45 degrees.

13. The analyzing device according to claim 11, wherein the light shield is formed with an opening for selectively exposing the first output area and the second entrance area.

14. The analyzing device according to claim 11, wherein the light shield comprises an annular part surrounding a periphery of at least one of the first output area and the second entrance area.

15. The analyzing device according to claim 2, wherein there is provided only a single measurement light-emitting unit, whereas there are provided a plurality of measurement light-receiving units, and wherein the plurality of measurement light-receiving units are arranged to surround the single measurement light-emitting unit.

16. The analyzing device according to claim 2, wherein there is provided a plurality of measurement light-emitting units, whereas there is provided only a measurement single light-receiving unit, and wherein the plurality of measurement light-emitting units are arranged to surround the single light-receiving unit.

17. The analyzing device according to claim 16, wherein the plurality of light-emitting units emit light of different peak wavelengths.

18. The analyzing device according to claim 2, wherein the measurement light-receiving unit is designed to receive scattered light reflected by the test tool.

19. The analyzing device according to claim 2, further comprising a wavelength selection portion for causing light reflected by the test tool to enter the measurement light-receiving unit after wavelength selection.

20. The analyzing device according to claim 2, further comprising a wavelength selection portion for outputting light emitted from the measurement light-emitting unit toward the test tool after wavelength selection.

21. The analyzing device according to claim 1, further comprising a detection light guide for defining a path of at least one of light traveling toward the test tool from the detection light-emitting unit and light traveling toward the detection light-receiving unit from the test tool.

22. The analyzing device according to claim 21, wherein the detection light guide comprises: a first entrance area for introducing light emitted from the detection light-emitting unit into the detection light guide; a first output area for outputting the light introduced into the detection light guide toward the test tool; a second entrance area for introducing reflection light from the test tool into the detection light guide; and a second output area for outputting the light reflected by the test tool and then introduced into the light guide toward the detection light-receiving unit;

wherein at least one of the first entrance area, the first output area, the second entrance area, and the second output area is arranged to refract light passing therethrough.

23. The analyzing device according to claim 21, wherein the detection light guide comprises a prism or a lens.

24. The analyzing device according to claim 23, wherein the prism or lens serving as the detection light guide is formed with recesses for fixedly fitting the detection light-emitting unit and the detection light-receiving unit, respectively, the prism or lens being further formed with a slit for preventing light from directly entering from the detection light-emitting unit into the detection light-receiving unit.

25. The analyzing device according to claim 21, wherein the detection light guide comprises a cylindrical lens or a Fresnel lens.

26. The analyzing device according to claim 21, wherein the detection light guide comprises: a lens having an irregular surface; and a cover that covers the irregular surface and makes an upper surface of the light guide flat.

27. The analyzing device according to claim 26, wherein the detection light guide comprises a Fresnel lens.

28. The analyzing device according to claim 21, wherein the detection light-emitting unit comprises a light-emitting diode.

29. The analyzing device according to claim 1, wherein the test tool is elongate in one direction, the conveying mechanism transferring the test tool from the placement area to the light-measuring area transversely to said one direction, the light-measuring mechanism being also movable along the test tool in said one direction.

* * * * *